United States Patent

Bernhard et al.

[11] Patent Number: 5,287,703
[45] Date of Patent: Feb. 22, 1994

[54] PROCESS FOR THE RECOVERY OF $C_2+$ OR $C_3+$ HYDROCARBONS

[75] Inventors: Dennis P. Bernhard, Allentown, Pa.; Michael H. Evans, Shepperton; Richard P. Freeman, Purley, both of England; Howard C. Rowles, Center Valley, Pa.

[73] Assignee: Air Products and Chemicals, Inc., Allentown, Pa.

[21] Appl. No.: 746,671

[22] Filed: Aug. 16, 1991

[51] Int. Cl.⁵ .................................................. F25J 3/02
[52] U.S. Cl. .......................................... 62/24; 62/23; 62/29; 62/31; 62/40
[58] Field of Search ................. 62/23, 24, 31, 40, 29, 62/18

[56] References Cited

U.S. PATENT DOCUMENTS

| | | | |
|---|---|---|---|
| 2,581,558 | 1/1952 | Ruhemann | 62/40 X |
| 2,823,523 | 2/1958 | Eakin et al. | 62/40 X |
| 3,242,682 | 3/1966 | English | 62/40 X |
| 3,592,015 | 7/1971 | Streich et al. | 62/40 X |
| 4,002,042 | 1/1977 | Pryor et al. | 62/28 |
| 4,230,469 | 10/1980 | Grimm et al. | 62/40 X |
| 4,272,270 | 6/1981 | Higgons | 62/24 |
| 4,356,014 | 10/1982 | Higgons | 62/28 |
| 4,507,133 | 3/1985 | Khan et al. | 62/69 |
| 4,526,596 | 7/1985 | Baggio | 62/40 |
| 4,608,068 | 8/1986 | Bauer et al. | 62/18 |
| 4,622,053 | 11/1986 | Tomlinson et al. | 62/26 |
| 4,664,687 | 5/1987 | Bauer | 62/29 |
| 4,675,036 | 6/1987 | Bauer | 62/18 |
| 4,689,063 | 8/1987 | Paradowski et al. | 62/40 X |
| 4,707,170 | 11/1987 | Ayres | 62/24 |
| 4,714,487 | 12/1987 | Rowles | 62/24 |
| 4,718,927 | 1/1988 | Bauer et al. | 62/39 |
| 4,738,699 | 4/1988 | Apffel | 62/40 X |
| 4,778,498 | 10/1988 | Hanson et al. | 62/40 X |
| 4,809,154 | 2/1989 | Newton | 62/40 X |
| 4,901,533 | 2/1990 | Fan et al. | 62/40 X |
| 4,987,744 | 1/1991 | Handley et al. | 62/40 X |
| 5,053,061 | 10/1991 | Chretien | 62/40 X |

Primary Examiner—John M. Sollecito
Assistant Examiner—C. Kilner
Attorney, Agent, or Firm—Robert J. Wolff; James C. Simmons; William F. Marsh

[57] ABSTRACT

A process for cooling, phase separating, rectifying and stripping a hydrocarbon containing feed gas stream to recover a heavy hydrocarbon product wherein a predominant amount of the refrigeration for the process is provided from a single loop vapor recompression refrigerator employing a mixed refrigerant.

6 Claims, 1 Drawing Sheet

PROCESS FOR THE RECOVERY OF $C_{2+}$ OR $C_{3+}$ HYDROCARBONS

TECHNICAL FIELD

The present invention relates to a process for the recovery of $C_{2+}$ or $C_{3+}$ hydrocarbons from a hydrocarbon containing stream using the sequential steps of cooling, phase separating, rectifying and stripping wherein the refrigeration necessary for such processing is derived predominantly from a single loop vapor recompression refrigerator employing a mixed refrigerant.

BACKGROUND OF THE INVENTION

A process for the recovery of a heavy hydrocarbon product (i.e., $C_{2+}$ or $C_{3+}$ hydrocarbons) from a hydrocarbon containing stream using the sequential steps of cooling, phase separating, rectifying and stripping is taught in the art. Specifically, U.S. Pat. No. 4,622,053 by Tomlinson, et al. discloses such a process. Tomlinson further discloses that the refrigeration for the process can be provided by a two-stage (two loop) cascade refrigerator (the preferred embodiment) or a single loop vapor recompression refrigerator employing a mixed refrigerant. It has now been found, however, that the efficiency of Tomlinson's cycle incorporating the sequential steps of cooling, phase separating, rectifying and stripping wherein the predominant amount of refrigeration is provided by a single loop vapor recompression refrigerator employing a mixed refrigerant can be significantly improved.

Other prior art of general relevance showing various individual steps that are relevant to the technical field of the present invention, including phase separating, rectifying via low temperature dephlegmation and stripping include: U.S. Pat. Nos. 4,002,042; 4,272,270; 4,356,014; 4,526,596; 4,507,133; 4,608,068; 4,664,687; 4,675,036; 4,707,170; 4,714,487 and 4,718,927.

SUMMARY OF THE INVENTION

The present invention claims an improvement to the prior art separation process for the recovery of a heavy hydrocarbon product from a hydrocarbon containing gas stream. The prior art separation process comprises:
 (a) cooling the gas stream to effect the partial condensation thereof;
 (b) phase separating the partially condensed gas stream into its vapor and liquid components in a phase separator;
 (c) rectifying the vapor component from step (b) by low temperature dephlegmation to produce a light gas stream and a heavy liquid stream; and
 (d) stripping the liquid component from step (b) and the heavy liquid stream from step (c) in a stripping column containing a reboiler wherein the bottoms stream from the stripping column is the heavy hydrocarbon product;
 (e) providing the predominant amount of the refrigeration for the process from a single loop vapor recompression refrigerator employing a mixed refrigerant;

The present invention claims an improvement to increase the energy efficiency of the above described prior art process. The improvement comprises:

(i) passing the liquid component from step (b) and the heavy liquid stream from step (c) directly to the stripping column of step (d);
 (ii) operating the stripping column at below ambient temperature;
 (iii) passing the overhead vapor from the stripping column directly to the phase separator of step (b) to be rectified with the vapor component from step (b); and
 (iv) using the mixed refrigerant employed in step (e) as a heating medium for the reboiler of the stripping column in order to provide at least a portion of the heat duty for the reboiler.

The present invention allows the feed gas stream to be processed at low pressure, for example, 40 to 200 psia, where the high relative volatility between the light and heavy components provides easier separations resulting in a lower energy of separation. Another major advantage of the present invention is that only one compressor (the single loop mixed refrigerant compressor) is required in most applications, resulting in significant capital savings.

DETAILED DESCRIPTION OF THE INVENTION

Figure 1:
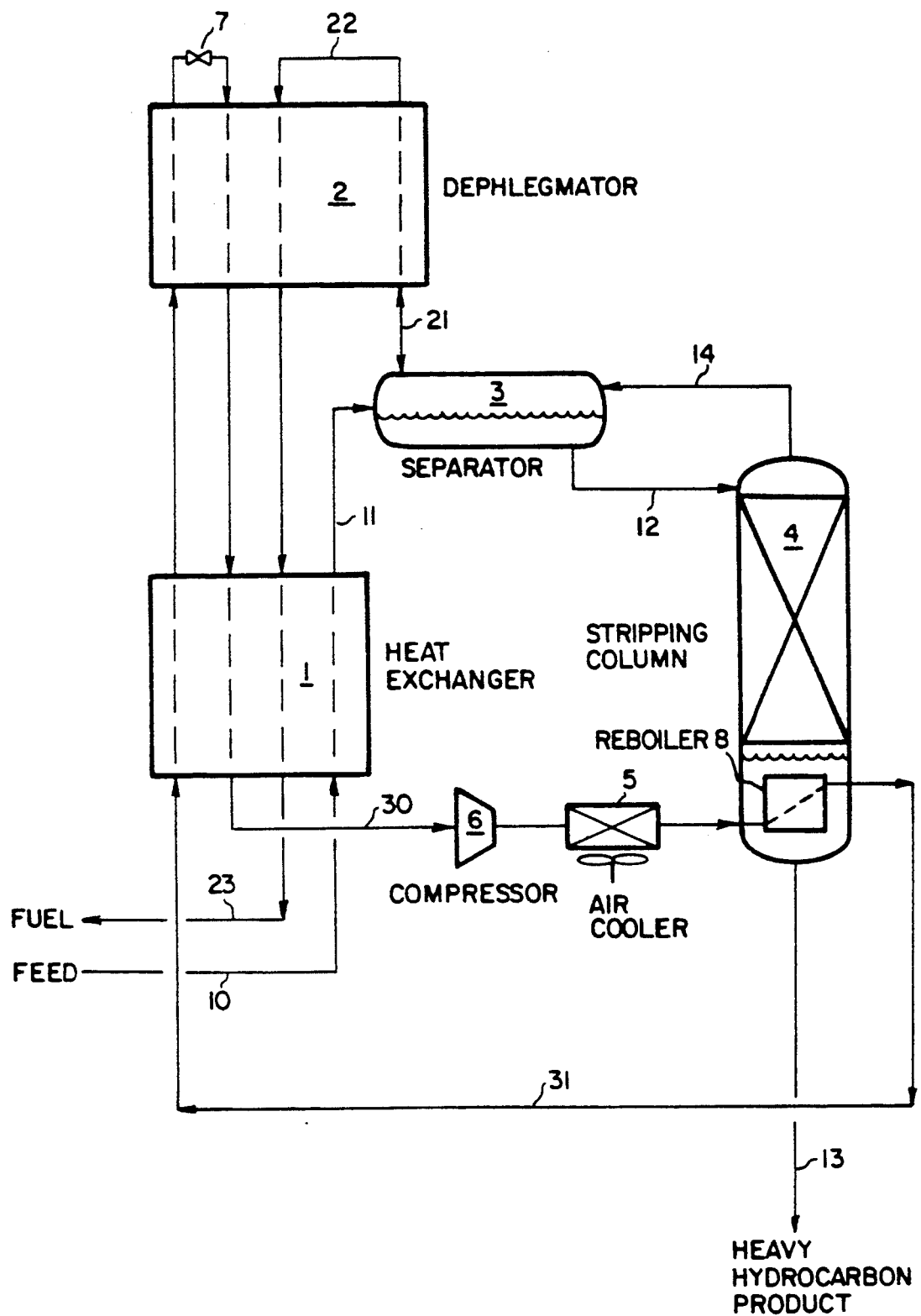
FIG. 1 is a flow diagram of one embodiment of the process of the present invention.

The present invention provides an efficient process for the recovery of $C_{2+}$ or $C_{3+}$ hydrocarbons from a hydrocarbon containing stream such as a refinery off-gas stream. The hydrocarbon containing stream can contain any number of non-hydrocarbon components such as hydrogen, nitrogen, carbon monoxide and carbon dioxide. The hydrocarbon components can include saturated and unsaturated hydrocarbons including methane, ethane, ethylene, propane, propylene, butane, butene, isobutane, pentane, pentene, hexane and potentially residual amounts of even heavier hydrocarbons. Throughout the text of this patent, saturated and unsaturated hydrocarbons are symbolically referenced as the $C_{x+}$ designate of the carbon number of the hydrocarbon. The "+" symbol is utilized to indicate that the carbon atom count constitutes the designated number placed in the "x" subscript and higher molecular weight compounds.

In the present invention, feed gas at relatively low pressure is cooled to an intermediate temperature, for example, $+30°$ F. to $-150°$ F. The condensed liquid is removed in a phase separator and the uncondensed vapor is further cooled and rectified in a dephlegmator to recover the remaining $C_{2+}$ or $C_{3+}$ hydrocarbons. The condensed liquids are fractionated in a stripping column operating at below ambient temperature to remove residual light components and increase the purity of the $C_{2+}$ or $C_{3+}$ hydrocarbon product. The purified hydrocarbons may be recovered as a liquid product or revaporized for refrigeration recovery.

The overhead vapor from the stripping column is returned to the phase separator and then to the dephlegmator to recover residual $C_{2+}$ or $C_{3+}$ hydrocarbons. The mixed refrigerant employed in the single loop vapor recompression refrigerator acts as a heating medium for the reboiler of the stripping column in order to provide at least a portion of the heat duty for the reboiler. If necessary, other streams, such as the feed and product streams, can be used to supply supplemental heat duty for the reboiler.

This process reduces both the power requirements and the capital cost for the separation and recovery of $C_2+$ or $C_3+$ hydrocarbons. It allows the feed gas stream to be processed at low pressure, for example, 40 to 200 psia, where the high relative volatility between the light and heavy components provides easier separations resulting in a lower energy of separation.

A major advantage of the process is that only one compressor, the single loop mixed refrigerant compressor, is required in most applications. Feed compression is not necessary; two separate compressors for a two-stage (two loop) cascade refrigerator are not required. The compression requirements for the process are consolidated into one machine, the mixed refrigerant compressor, resulting in significant capital savings. In addition, the rectification achieved in the dephlegmator minimizes the quantity of light components entering the stripping column, resulting in a smaller column and more efficient fractionation.

The present invention is an improvement to the prior art cycle for recovering heavy hydrocarbons (i.e., $C_2+$ or $C_3+$ hydrocarbons) from a hydrocarbon containing stream. The prior art cycle is shown in FIG. 2 of U.S. Pat. No. 4,622,053 by Tomlinson, et al. and comprises the sequential steps of cooling, phase separating, rectifying and stripping. Refrigeration for the preferred embodiment of the prior art cycle is provided by a two-stage (two loop) cascade refrigerator. However, the Tomlinson patent recites in column 6, lines 38 thru 43, that, "The two-stage cascade refrigerator employed in the process described in FIG. 2 may be replaced by some other form of external refrigeration, if desired. For example, a single loop vapour compression refrigerator employing a mixed refrigerant may be employed [as in the present invention] but the power savings will not be so great."

The significant and unexpected increase in efficiency of the present invention over the prior art cycle is derived from the following improvements to the prior art cycle:

1. In the prior art cycle, the liquid component from the phase separating step and the liquid component from the rectification step are mixed and warmed by indirect heat exchange with the feed gas mixture prior to sending such liquid components to the stripping column; in the present invention, these liquid components are passed directly to the stripping column, without warming.

2. In the prior art cycle, the stripping column is operated at or above ambient temperature; in the present invention the stripping column is operated below ambient temperature.

3. In the prior art cycle, the overhead vapor from the stripping column is mixed with the incoming feed and cooled prior to being directed to the phase separator; in the present invention, this vapor component is passed directly to the phase separator, without cooling.

4. In the prior art cycle, hot oil or low pressure steam is used as a heating medium for the reboiler of the stripping column; in the present invention, the mixed refrigerant is used as the heating medium for the reboiler of the stripping column in order to provide at least a portion of the heat duty for the reboiler.

Implementation of the above improvements to the prior art cycle significantly increases the efficiency of the separation process. As shown in the following Table 1, the present invention requires 19% less power than the preferred embodiment of the prior art cycle for recovering the $C_3+$ hydrocarbons from a typical refinery off gas stream. These power savings are even more impressive considering that the Tomlinson patent, as noted above, stated a power penalty would be incurred when substituting a single loop vapor recompression refrigerator employing a mixed refrigerant (as in the present invention) in place of the preferred embodiment's two-stage (two loop) cascade refrigerator. Both the present invention and the prior art cycle achieve 95% recovery of propane and 100% recovery of $C_4+$ components.

TABLE 1

| RELATIVE PERFORMANCE OF PRESENT INVENTION vs. TOMLINSON PROCESS* | | |
|---|---|---|
| | Present Invention | Tomlinson Process* |
| Feed (lb moles/hr)** | 1654 | 1654 |
| Propane Recovery | 95% | 95% |
| $C_4+$ Recovery | 100% | 100% |
| Total Power (HP) | 1660 | 2050 |

*As shown in FIG. 2 of U.S. Pat. No. 4,622,053 by Tomlinson, et al.
**The feed is at 80° F. and 105 psia and contains 54.1% hydrogen, 0.2% carbon dioxide, 14.2% methane, 11.7% ethane, 0.8% propylene, 10.9% propane, 3.2% isobutane, 3.2% butane, 1.4% pentane and 0.3% hexane.

One embodiment of the present invention will now be described in detail as it relates to the recovery of $C_3+$ hydrocarbons from a typical refinery off-gas stream. Referring to FIG. 1, a feed gas is introduced in line 10 at 80° F. and 105 psia containing 54.1% hydrogen, 0.2% carbon dioxide, 14.2% methane, 11.7% ethane, 0.8% propylene, 10.9% propane, 3.2% isobutane, 3.2% butane, 1.4% pentane and 0.3 hexane. The feed gas in line 10 is cooled in heat exchanger 1. The feed gas is partially condensed as it exits in line 11 at a temperature of $-10°$ F. and a pressure of 100 psia. It is introduced into a phase separator vessel 3 to produce a heavy liquid stream containing heavy hydrocarbons in line 12 and a vapor stream containing light feed gas components in line 21. The vapor stream in line 21 ascends a refluxing heat exchanger, or dephlegmator 2, wherein it is partially condensed and the heavy condensed portion of the stream descends the heat exchange passageways to act as a reflux to rectify the vapor stream in line 21. The condensed portion of the stream is returned to phase separator vessel 3 to be combined with the stream initially phase separated as the heavy liquid stream in line 12. The light components which exit overhead from the dephlegmator 2 are removed in line 22 at $-113°$ F. and 99 psia. This stream in line 22 is returned thru dephlegmator 2 and heat exchanger 1 and, after being re-warmed, is removed as a fuel stream in line 23 at 110° F. and 90 psia containing 67.0% hydrogen, 0.3% carbon dioxide, 17.5% methane, 14.2% ethane, 0.3% propylene, and 0.7% propane.

The heavy liquid stream is passed thru line 12 into stripping column 4. The stripping column is operated with a reboiler 8 in its bottom. The heavy hydrocarbon product containing $C_3+$ hydrocarbons is derived from the bottom of the stripping column in line 13 at 80° F. and 101 psia containing 1.0% ethane, 2.9% propylene, 54.0% propane, 16.4% isobutane, 16.6% butane, 7.5% pentane and 1.6% hexane. The overhead vapor from the stripping column is removed in line 14 and returned to phase separator 3 to be rectified in dephlegmator 2 to recover residual $C_3+$ hydrocarbons.

The refrigeration necessary to operate the process described and illustrated in FIG. 1 is derived from a single loop vapor recompression refrigerator employing a mixed refrigerant. The mixed refrigerant can be derived from any number of components but is generally selected from the components comprising the feed gas. In FIG. 1, the mixed refrigerant consists of 5.8% methane, 50.4% ethane and 43.8% butane. Referring to FIG. 1, the mixed refrigerant in line 30 is at a temperature of 110° F. and a pressure of 17 psia. It is recompressed in compressor 6 to 395 psia and partially condensed in air cooler 5 and in the reboiler of the stripping column. The partially condensed, high pressure mixed refrigerant stream exits the reboiler in line 31 at 115° F. and is further condensed and cooled to −118° F. in heat exchanger 1 and dephlegmator 2, flashed to 20 psia in valve 7 and partially revaporized in dephlegmator 2 to provide low temperature refrigeration. The low pressure mixed refrigerant is then further warmed and vaporized in heat exchanger 1 and returned to compressor 6 in line 30 at 110° F. and 17 psia.

Although not shown in FIG. 1, it is also possible to obtain supplemental refrigeration for the process through expansion of the feed gas stream. For example, the light components exiting the top of the dephlegmator in line 22 could be expanded prior to rewarming in the dephlegmator or after rewarming in the dephlegmator.

Another source of supplemental refrigeration which may be utilized is revaporization of the heavy hydrocarbon product in line 13. When the heavy hydrocarbon product is not required as a liquid stream, the heavy hydrocarbon product could be revaporized in the dephlegmator 2 or in the heat exchanger 1 to provide supplemental refrigeration.

The single loop vapor recompression refrigerator employs a mixed refrigerant to provide the predominant amount of refrigeration for the process. The mixed refrigerant can be made up from relatively pure components, if available, or from a suitable mixture of components obtained from the processing of the feed gas. For example, a suitable mixed refrigerant composition might be obtained by mixing vapor obtained from line 14 or line 21 with liquid obtained from line 12 or line 13 in appropriate proportions.

The composition of the mixed refrigerant and its condensing and vaporizing pressure levels are selected to provide thermodynamically efficient temperature differences between the process streams and the mixed refrigerant streams in the heat exchangers and in the dephlegmator. The mixed refrigerant is compressed to a sufficiently high pressure that it can be at least partially condensed with a combination of refrigeration sources available from cooling water or air coolers, from the reboiler of the stripping column and from rewarming of the process streams. The mixed refrigerant may be partially condensed or it may be totally condensed and subcooled prior to flashing and vaporizing at lower pressure for refrigeration supply.

For convenience, the vapor and liquid portions of the single loop mixed refrigerant stream may be condensed and cooled separately or vaporized and warmed separately in any of the heat exchangers or in the dephlegmator. The mixed refrigerant may also be vaporized and warmed at more than one pressure level for refrigeration supply to reduce recompression energy.

The present invention has been described with reference to a specific embodiment thereof. This embodiment should not be seen as a limitation of the scope of the present invention; the scope of such being ascertained by the following claims.

We claim:

1. In a low temperature separation process for the recovery of a heavy hydrocarbon product from a hydrocarbon containing gas stream comprising:
   (a) cooling the gas stream to effect the partial condensation thereof;
   (b) phase separating the partially condensed gas stream into its vapor and liquid components in a phase separator;
   (c) rectifying the vapor component from step (b) by low temperature dephlegmation to produce a light gas stream and a heavy liquid stream; and
   (d) stripping the liquid component from step (b) and the heavy liquid stream from step (c) in a stripping column containing a reboiler wherein the bottoms stream from the stripping column is the heavy hydrocarbon product;
   (e) providing the predominant amount of the refrigeration for the process from a single loop vapor recompression refrigerator employing a mixed refrigerant;

the improvement for increasing the efficiency of said separation process comprising:
   (i) passing the liquid component from step (b) and the heavy liquid stream from step (c) directly to the stripping column of step (d);
   (ii) operating the stripping column at below ambient temperature;
   (iii) passing the overhead vapor from the stripping column directly to the phase separator of step (b) to be rectified with the vapor component from step (b); and
   (iv) using the mixed refrigerant employed in step (e) as a heating medium for the reboiler of the stripping column in order to provide at least a portion of the heat duty for the reboiler.

2. The separation process in accordance with claim 1 wherein the hydrocarbon containing gas stream contains hydrogen, nitrogen, carbon monoxide, carbon dioxide, methane and $C_2+$ hydrocarbons.

3. The separation process in accordance with claim 2 wherein the heavy hydrocarbon product contains $C_2+$ hydrocarbons.

4. The separation process in accordance with claim 2 wherein the heavy hydrocarbon product contains $C_3+$ hydrocarbons.

5. The separation process in accordance with claim 1 wherein the hydrocarbon containing gas stream is at a pressure between 40 and 200 psia and wherein said separation process involves no compression of said gas stream.

6. The separation process in accordance with claim 1 wherein the components of the mixed refrigerant are obtained from the hydrocarbon containing gas stream.

* * * * *